United States Patent
Barten et al.

(10) Patent No.: US 12,031,141 B2
(45) Date of Patent: Jul. 9, 2024

(54) TOMATO PLANTS WITH IMPROVED DISEASE RESISTANCE

(71) Applicant: Seminis Vegetable Seeds, Inc., St. Louis, MO (US)

(72) Inventors: Johannes Hendrikus Maria Barten, Roquetas de Mar (ES); Susana Garcia-Andres, Almeria (ES); Benjamin C. Hunter, Zuid-Holland (NL); Francisco Monci Marin, Almeria (ES); Maria Belen Salleres Neira, Almeria (ES)

(73) Assignee: SEMINIS VEGETABLE SEEDS, INC., St. Louis, MO (US)

( * ) Notice: Subject to any disclaimer, the term of this patent is extended or adjusted under 35 U.S.C. 154(b) by 0 days.

(21) Appl. No.: 17/403,380

(22) Filed: Aug. 16, 2021

(65) Prior Publication Data

US 2022/0064663 A1    Mar. 3, 2022

Related U.S. Application Data

(60) Provisional application No. 63/070,137, filed on Aug. 25, 2020.

(51) Int. Cl.
| | |
|---|---|
| *C12N 15/82* | (2006.01) |
| *A01H 1/00* | (2006.01) |
| *A01H 1/02* | (2006.01) |
| *A01H 6/82* | (2018.01) |

(52) U.S. Cl.
CPC ......... *C12N 15/8283* (2013.01); *A01H 1/021* (2021.01); *A01H 1/126* (2021.01); *A01H 6/825* (2018.05)

(58) Field of Classification Search
CPC ..... C12N 15/8283; A01H 1/021; A01H 6/825
See application file for complete search history.

(56) References Cited

U.S. PATENT DOCUMENTS 6,100,449 A * 8/2000 Fluhr ................. C12N 15/8282
                                                          800/290

FOREIGN PATENT DOCUMENTS

| WO | 2018101824 | 6/2018 |
| WO | 2020018783 | 1/2020 |

OTHER PUBLICATIONS

Stam et al., 2019, The de novo reference genome and transcriptome assemblies of the wild tomato species *Solanum chilense* highlights birth and death of NLR genes between tomato species. G3: Genes, Genomes, Genetics, 9(12), 3933-3941. (Year: 2019).*

Fernandez-Pozo et al., 2015, The Sol Genomics Network (SGN)—from genotype to phenotype to breeding. Nucleic acids research, 43(D1), D1036-D1041. (Year: 2015).*

Wei, C., Kuang, H., Li, F., & Chen, J. (2014). The I-2 resistance gene homologues in Solanum have complex evolutionary patterns and are targeted by miRNAs. BMC genomics, 15(1), 1-14. (Year: 2014).*

Pérez de Castro et al., 2013, Genetic control and mapping of Solanum chilense LA1932, LA1960 and LA1971-derived resistance to Tomato yellow leaf curl disease. Euphytica, 190(2), 203-214. (Year: 2013).*

Li et al., 2018, Linkage between the I-3 gene for resistance to Fusarium wilt race 3 and increased sensitivity to bacterial spot in tomato. Theoretical and applied genetics, 131(1), 145-155. (Year: 2018).*

Ji et al., 2009, Toward fine mapping of the Tomato yellow leaf curl virus resistance gene Ty-2 on chromosome 11 of tomato. HortScience, 44(3), 614-618. (Year: 2009).*

Kim et al., 2011, Application of disease resistance markers for developing elite tomato varieties and lines. Horticultural Science & Technology, 29(4), 336-344. (Year: 2011).*

SolGenomics Database search for TG26. https://solgenomics.net/. Accessed Aug. 28, 2023. (Year: 2023).*

SolGenomics Database search for TG105A. https://solgenomics.net/. Accessed Aug. 28, 2023. (Year: 2023).*

Garcia-Cano et al., Resistance to tomato chlorosis virus in wild tomato species that impair virus accumulation and disease symptom expression, Phytopathology 100: 582-592, 2010.

Gonzalez-Arcos et al., Identification of genetic sources with attenuated tomato chlorosis virus-induced symptoms in Solanum (section Lycopersicon) germplasm, Euphytica 214(178): 1-16, 2018.

Mansilla-Cordova et al., Screening tomato genotypes for resistance and tolerance to tomato chlorosis virus, Plant Pathology 67: 1231-1237, 2018.

Ori et al., A genomic search for the gene conferring resistance to fusarium wilt in tomato, Euphytica 79: 201-204, 1994.

Wisler et al, Tomato chlorosis virus: a new whitefly-transmitted phloem-limited, bipartite closterovius of tomato, Phytopathlogy 88(5): 402-409, 1998.

International Search Report and Written Opinion regarding International App. No. PCT/US2021/046180, dated Dec. 16, 2021.

Jin et al., Successful generation of anti-ToCV and TYLCV transgenic tomato plants by RNAi, Biologia Plantarum 64:490-496, 2020.

(Continued)

*Primary Examiner* — David H Kruse
*Assistant Examiner* — Santosh Sharma
(74) *Attorney, Agent, or Firm* — Dentons US LLP; Alissa Eagle

(57) ABSTRACT

Tomato plants exhibiting resistance to tomato chlorosis virus and *Fusarium oxysporum* f. sp. *lycopersici* race 2 are provided, together with methods of producing, identifying, or selecting plants or germplasm with a tomato chlorosis virus and *Fusarium oxysporum* f. sp. *lycopersici* race 2 resistance phenotype and lacking an undesirable cold sensitivity trait. Such plants include tomato plants comprising recombinant genomic regions conferring disease resistance. Compositions, including novel polymorphic markers for detecting plants comprising introgressed disease resistance alleles, are further provided.

10 Claims, 1 Drawing Sheet

Specification includes a Sequence Listing.

(56) References Cited

OTHER PUBLICATIONS

Li et al., Linkage between the I-3 gene for resistance to Fusarium wilt race 3 and increased sensitivity to bacterial spot in tomato, Theoretical and Applied Genetics 131:145-155, 2018.
Tzanetakis et al., Epidemiology of criniviruses: an emerging problem in world agriculture, Frontiers in Microbiology 4 (119):1-15, 2013.

\* cited by examiner

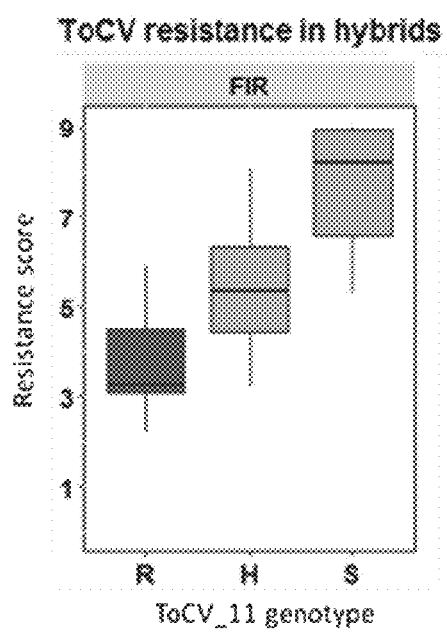

TOMATO PLANTS WITH IMPROVED DISEASE RESISTANCE

CROSS-REFERENCE TO RELATED APPLICATIONS

This application claims the priority of U.S. Provisional Appl. Ser. No. 63/070,137, filed Aug. 25, 2020, the entire disclosure of which is incorporated herein by reference.

INCORPORATION OF SEQUENCE LISTING

A sequence listing containing the file named "SEMB045US-revised ST25.txt" which is 6.3 kilobytes (measured in MS-Windows®) and created on Jul. 18, 2023, and comprises 20 sequences, is incorporated herein by reference in its entirety.

FIELD OF THE INVENTION

The present invention relates to the field of plant breeding and more specifically to methods and compositions for producing tomato plants exhibiting improved disease resistance without linked deleterious traits.

BACKGROUND

Disease resistance is an important trait in agriculture, particularly for the production of food crops. Although disease resistance alleles have been identified in tomato, efforts to introduce these alleles into cultivated lines have been hindered by a lack of specific markers linked to the alleles, as well as the presence of deleterious alleles genetically linked to disease resistance alleles that lead to an unacceptable reduction in yield, fruit size, and fruit quality. The use of marker-assisted selection (MAS) in plant breeding has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis, and an often incomplete understanding of the genetic background underlying expression of a desired phenotype. In the absence of accurate and validated markers for use in MAS, it may not be feasible to produce new plant lines exhibiting certain disease resistance phenotypes and acceptable yield, fruit size, and fruit quality.

SUMMARY

In one aspect, the present invention provides a *Solanum lycopersicum* plant comprising a recombinant chromosomal segment on chromosome 11, wherein said chromosomal segment comprises a tomato chlorosis virus (ToCV) resistance allele from *Solanum chilense* that confers to said plant an increased resistance to ToCV compared to a plant not comprising said allele, and wherein: (a) said chromosomal segment lacks an allele genetically linked to said ToCV resistance allele that confers cold sensitivity when present in a plant; or, (b) said chromosomal segment comprises a *Fusarium oxysporum* f. sp. *lycopersici* (Fol) race 2 resistance allele from *Solanum pimpinellifolium* that confers to said plant increased resistance to Fol race 2 compared to a plant not comprising said allele, wherein said Fol race 2 resistance allele is in cis linkage with said ToCV resistance allele. In some embodiments, said ToCV resistance allele is further defined as located within a chromosomal segment on chromosome 11 flanked by marker locus M1 (SEQ ID NO:6) and marker locus M3 (SEQ ID NO:16) in said plant. In other embodiments, said plant is homozygous for said ToCV resistance allele. In certain embodiments, a representative sample of seed comprising said chromosomal segment has been deposited under NCMA Accession No. 202007005. In some embodiments, said Fol race 2 resistance allele is located within a chromosomal segment flanked by marker locus M4 (SEQ ID NO:1) and marker locus M1 (SEQ ID NO:6) on chromosome 11 in said plant.

In addition, the present invention provides a cell, seed, or plant part of a *Solanum lycopersicum* plant comprising a recombinant chromosomal segment on chromosome 11, wherein said chromosomal segment comprises a tomato chlorosis virus (ToCV) resistance allele from *Solanum chilense* that confers to said plant an increased resistance to ToCV compared to a plant not comprising said allele, and wherein: (a) said chromosomal segment lacks an allele genetically linked to said ToCV resistance allele that confers cold sensitivity when present in a plant; or, (b) said chromosomal segment comprises a *Fusarium oxysporum* f. sp. *lycopersici* (Fol) race 2 resistance allele from *Solanum pimpinellifolium* that confers to said plant increased resistance to Fol race 2 compared to a plant not comprising said allele, wherein said Fol race 2 resistance allele is in cis linkage with said ToCV resistance allele, wherein the cell, seed, or plant part comprises said recombinant chromosomal segment. In some embodiments, a representative sample of seed comprising said chromosomal segment has been deposited under NCMA Accession No. 202007005.

The present invention provides a recombinant DNA segment comprising a tomato chlorosis virus (ToCV) resistance allele from *Solanum chilense* that confers increased resistance to ToCV and lacks an allele genetically linked thereto that confers cold sensitivity when present, wherein said DNA segment comprises a *Fusarium oxysporum* f. sp. *lycopersici* (Fol) race 2 resistance allele from *Solanum pimpinellifolium* that confers increased resistance to Fol race 2, and wherein said Fol race 2 resistance allele in cis linkage with said ToCV resistance allele. In some embodiments, said recombinant DNA segment comprises a sequence selected from the group consisting of SEQ ID NOs:1, 6, 11, and 16. In other embodiments, said recombinant DNA segment is further defined as comprised within a plant, plant part, plant cell, or seed. In further embodiments, a representative sample of seed comprising said chromosomal segment has been deposited under NCMA Accession No. 202007005.

The present invention also provides a method of producing a tomato plant with improved tomato chlorosis virus (ToCV) resistance, comprising introgressing into said plant at least one ToCV resistance allele from *Solanum chilense* within a recombinant chromosomal segment flanked in the genome of said plant by marker locus M1 (SEQ ID NO:6) and marker locus M3 (SEQ ID NO:16) on chromosome 11, wherein said introgressed ToCV resistance allele confers to said plant increased resistance to ToCV compared to a plant not comprising said allele, and wherein said recombinant chromosomal segment lacks a deleterious allele genetically linked thereto that confers a cold sensitivity phenotype when present, and wherein said introgressing comprises marker-assisted selection. In some embodiments, said introgressing comprises backcrossing or assaying for said ToCV resistance. In other embodiments, said introgressing comprises: a) crossing a plant comprising said chromosomal segment with itself or with a tomato plant of a different genotype to produce at least a first progeny plant; and b) selecting a progeny plant comprising said chromosomal segment. In some embodiments, marker-assisted selection comprises detecting a marker locus genetically linked to said ToCV resistance allele selected from the group consisting of: marker locus M1 (SEQ ID NO:6), marker locus M2 (SEQ ID NO:11), and marker locus M3 (SEQ ID NO:16). In other embodiments, said progeny plant is an $F_2$-$F_6$ progeny plant. The present invention further provides tomato plants obtainable by the methods provided herein.

The present invention also provides a method of selecting a tomato plant exhibiting resistance to tomato chlorosis virus (ToCV) and *Fusarium oxysporum* f. sp. *lycopersici* (Fol) race 2, comprising: a) crossing a *Solanum lycopersicum* plant comprising a recombinant chromosomal segment on chromosome 11, wherein said chromosomal segment comprises a tomato chlorosis virus (ToCV) resistance allele from *Solanum chilense* that confers to said plant an increased resistance to ToCV compared to a plant not comprising said allele, and wherein: (a) said chromosomal segment lacks an allele genetically linked to said ToCV resistance allele that confers cold sensitivity when present in a plant; or, (b) said chromosomal segment comprises a *Fusarium oxysporum* f. sp. *lycopersici* (Fol) race 2 resistance allele from *Solanum pimpinellifolium* that confers to said plant increased resistance to Fol race 2 compared to a plant not comprising said allele, wherein said Fol race 2 resistance allele is in cis linkage with said ToCV resistance allele with itself or with a second tomato plant of a different genotype to produce one or more progeny plants; and b) selecting a progeny plant comprising said chromosomal segment. In some embodiments, selecting said progeny plant comprises detecting a marker locus genetically linked to said chromosomal segment. In other embodiments, selecting said progeny plant comprises detecting a marker genetically linked to marker locus M4 (SEQ ID NO:1), marker locus M1 (SEQ ID NO:6), marker locus M2 (SEQ ID NO:11), or marker locus M3 (SEQ ID NO:16). In some embodiments, said progeny plant is an $F_2$-$F_6$ progeny plant. In other embodiments, producing said progeny plant comprises backcrossing.

BRIEF DESCRIPTION OF THE DRAWINGS

FIG. 1: Shows data indicating that resistance to ToCV is additive. The genotypes on the x-axis are: S=homozygous sensitive, H=heterozygous for ToCV resistance, R=homozygous for ToCV resistance. The disease resistance score on the Y-axis ranges from 1 to 9, where 1 is highly resistant to ToCV and 9 completely sensitive to ToCV.

DETAILED DESCRIPTION

Tomato (*Solanum lycopersicum*) is an economically important vegetable crop that is grown worldwide. Many pathogens affect tomato plants by reducing production for tomato growers. While pesticidal measures are often used to control pathogens, consumers increasingly demand reduced use of pesticidal chemicals in the food they eat. This trend has put increased emphasis on the development of disease resistant tomato varieties by breeders.

An increasingly commercially important pathogen is tomato chlorosis virus (ToCV), which after its discovery in the late 1990s, has spread across the world to most important tomato producing regions. ToCV is a member of the genus *Crinivirus* in the family Closteroviridae and is spread by whitefly vectors. At least three whitefly species have been known to transmit ToCV. At the same time, ToCV can infect not only tomato, but also potato and pepper, along with several wild hosts, such as *Physalis ixocarpa*, *Physalis peruviana*, *Solanum nigrum*, and *Datura stramonium*. The virus is very hard to eradicate when it arrives in an area due to its broad vector transmissibility and wide host range. Currently, ToCV is managed through vector control and preventative cultural practices. However, these measures have had limited success in tomato production areas. Therefore, there is a need to find genetic resistance against ToCV and develop resistant commercial varieties. Several studies have found wild tomato relatives with levels of ToCV resistance that could be sources of resistance for commercial varieties. However, resistance to this virus is not widely spread in commercial germplasm because the ToCV resistance has thus far been associated with a deleterious cold sensitivity phenotype preventing the trait from being used in important tomato growing markets during the long-crop season. Furthermore, ToCV is an additive resistance such that when in heterozygous form it does not meet the required resistance level that tomato growers need. Therefore, the ToCV resistance locus needs to be deployed homozygously. Homozygous deployment of the ToCV resistance locus precludes use of the *Fusarium oxysporum* f sp. *lycopersici* (Fol) race 1 (race 2 ex-EU) resistance gene I-2 in the same plant, as it has been believed that the I-2 locus is located in the same place on the chromosome as the ToCV resistance locus.

*Fusarium* wilt is a disease of tomato plants that is caused by the soil-born fungus *Fusarium oxysporum* f sp. *lycopersici* (Fol). The Fol population can be divided into three distinct races, wherein resistance to each race is conferred by race-specific resistance loci. Resistance to Fol race 2 in tomato is conferred by the I-2 locus, which is introgressed from the wild tomato relative *Solanum pimpinellifolium*. The I-2 locus has been widely used in breeding and is available in many elite and commercial tomato varieties. This locus was mapped in 1994 and is located in close proximity to the TG105 RFLP marker on the end of chromosome 11 of the public tomato genome map version SL2.50 (The Tomato Genome Consortium; *Nature* 485:635-641, 2012; publically available on the internet through solgenomics.net).

The commercial tomato variety Elenita was found to be partially resistant to ToCV. Examination of the parent lines of this variety showed that one of the parents was resistant to ToCV. This resistance was found to be additive and resulted in cold sensitive plants. Genetic mapping showed that the resistance was monogenic and located on the end of chromosome 11 of the public tomato genome map version SL2.50. This region overlaps with the I-2 locus that confers Fol race 2 resistance. The breeders found that it was not possible to recombine the I-2 locus with the ToCV resistance locus and concluded that these two traits were linked in repulsion, meaning that breeders would only be able to deploy both traits heterozygously in a given variety. However, since the commercially desirable level of ToCV resistance is achieved when the ToCV resistance locus is homozygous, it was thus necessary to develop lines that combined ToCV resistance and the I-2 locus in cis linkage to allow breeders to deploy homozygous ToCV resistance.

Detailed fine mapping of the ToCV resistance locus reduced the introgression to an interval of 0.6 cM, which removed the deleterious cold sensitivity phenotype locus. This interval still overlapped with the I-2 locus, making it unlikely that recombinants would be found. Surprisingly, the present inventors identified two tomato lines that had the marker for the ToCV resistance locus and the marker for the I-2 locus on the same chromosome. Phenotypic testing confirmed that these lines were indeed resistant to both ToCV and Fol race 2. The ToCV locus was situated between marker locus M1, a SNP marker with a [C/T] change at 54,914,243 bp on chromosome 11 of the public tomato genome map version SL2.50, and M3, a SNP marker with a [A/T] change at 55,443,272 bp on chromosome 11 of the public tomato genome map version SL2.50. Interstitial marker locus M2, a SNP marker with a [A/G] change at 55,135,473 bp on chromosome 11 of the public tomato genome map version SL2.50, can also be used to select for the ToCV resistance locus. The I-2 locus is flanked by marker locus M1 and marker locus M4, a SNP marker with a [G/T] change at 54,895,724 bp on chromosome 11 of the public tomato genome map version SL2.50. Marker locus M1 may be used to select for the I-2 locus. The public genome of tomato is available at for example, the Solanaceae Genomics Network (solgenomics.net), and one skilled in the art would understand that the marker sequences provided for the first time in the instant application could be located on any version (or later version) of the public genome.

In certain embodiments, tomato plants are provided herein comprising an introgressed allele on chromosome 11, wherein said introgressed allele confers to said plant increased resistance to ToCV compared to a plant not comprising said allele. In further embodiments, said plant lacks a further allele, genetically linked to said introgressed allele, that confers a cold sensitivity phenotype when present.

Further provided herein are reduced recombinant introgressions comprising a genomic interval between marker locus M1 (SEQ ID NO:6) and marker locus M3 (SEQ ID NO:16) on chromosome 11, wherein said reduced genomic interval lacks deleterious cold sensitivity alleles associated with larger ToCV resistance introgressions.

In other embodiments, the invention provides plants comprising one or more of the novel recombinant introgressions provided herein. These novel introgressions provide robust resistance both ToCV and Fol race 2, while avoiding the reduction in performance characteristics associated with conventional introgressions. Methods of producing the plants described herein are further provided. In certain embodiments, the invention provides tomato line CHI-1120-0340 comprising an exemplary chromosomal segment described herein, a sample of the seed of which has been deposited NCMA Accession No. 202007005.

The invention further provides novel trait-linked markers which can be used to produce plants comprising novel recombinant introgressions on chromosome 11 conferring both ToCV and Fol race 2 resistance as described herein. In particular embodiments, the invention provides the markers shown in Table 1.

The invention provides methods of producing or selecting a tomato plant exhibiting resistance to ToCV and Fol race 2 comprising: a) crossing a tomato plant provided herein with itself or with a second tomato plant of a different genotype to produce one or more progeny plants; and b) selecting a progeny plant comprising said first introgressed allele and/or said second introgressed allele. In some embodiments, methods of the invention comprise selecting a progeny plant by detecting a marker genetically linked to marker locus M4 (SEQ ID NO:1), marker locus M1 (SEQ ID NO:6), marker locus M2 (SEQ ID NO:11), or marker locus M3 (SEQ ID NO:16).

Because genetically diverse plant lines can be difficult to cross, the introgression of ToCV resistance alleles into cultivated lines using conventional breeding methods could require prohibitively large segregating populations for progeny screens with an uncertain outcome. Marker-assisted selection (MAS) is therefore essential for the effective introgression of ToCV resistance alleles into elite cultivars. However, previously known markers for ToCV resistance have failed to discriminate between donor DNA conferring disease resistance and donor DNA conferring deleterious traits. This has been further complicated by the previous inability to resolve the specific regions associated with disease resistance. For the first time, the present invention enables effective MAS by providing improved and validated markers for detecting genotypes associated with disease resistance without the need to grow large populations of plants to maturity in order to observe the phenotype.

I. Genomic Regions, Alleles, and Polymorphisms Associated with Disease Resistance in Tomato Plants The invention provides novel introgressions of one or more alleles associated with ToCV and Fol race 2 resistance without the detrimental cold sensitivity phenotypes in tomato plants, together with polymorphic nucleic acids and linked markers for tracking the introgressions during plant breeding.

Tomato lines exhibiting ToCV resistance and Fol race 2 resistance, respectively, are known in the art and may be used together with the novel trait-linked markers provided herein in accordance with certain embodiments of the invention. For example, the wild tomato accession *Solanum chilense* line LA1932, which is available from the Tomato Genetics Resource Center at UC-Davis, California, USA, can be used as a source for ToCV resistance. In addition, the commercial varieties Elenita and Carmencita may also be used as sources for ToCV resistance. There are many publicly available tomato varieties that may be used as a source for the I-2 locus. In principle, any commercial variety for which the breeder claims Fol 0,1 (ex-EU Fol 1,2) resistance will have the I-2 locus. Specifically, the following commercial varieties could be used as a donor for the I-2 locus: Merlice, Torero, SV7011TG, SV1882TH, Bateyo, Carambola, Admiro, Endeavor RZ F1 (72-487), Arvento RZ F1 (72-375), Batistuta, Cherlino, or Annamay.

Using the improved genetic markers and assays of the invention, the present inventors were able to successfully identify novel reduced introgressions from *Solanum chilense* that confer ToCV resistance to the plant with fewer deleterious traits when introgressed into a cultivated line. The novel introgressions provided herein confer robust resistance to ToCV and Fol race 2, while avoiding the cold sensitivity phenotype seen with conventional introgressions. The invention therefore represents a significant advance in the art.

II. Introgression of Genomic Regions Associated with ToCV and Fol Race 2 Resistance Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a ToCV and Fol race 2 resistant plant into a cultivated line. The invention further provides markers for identifying and tracking the novel introgressions disclosed herein during plant breeding, including the markers set forth in Table 1.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistant phenotype.

Tomato plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Tomato plants comprising an introgressed region comprising regions closely linked to or adjacent to the genomic regions and markers provided herein and associated with a disease resistance phenotype are also provided.

III. Development of Disease Resistant Tomato Varieties

For most breeding objectives, commercial breeders work with germplasm that is "cultivated," "cultivated type," or "elite." These cultivated lines may be used as recurrent parents or as a source of recurrent parent alleles during breeding. Cultivated or elite germplasm is easier to breed because it generally performs well when evaluated for horticultural performance. Many cultivated tomato types have been developed and are known in the art as being agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. Non-cultivated germplasm may be used as a source of donor alleles during breeding. However, this approach generally presents significant difficulties due to fertility problems associated with crosses between diverse lines, and genetically linked deleterious alleles from the non-cultivated parent. For example, non-cultivated tomato types can provide alleles associated with disease resistance. However, these non-cultivated types may have poor horticultural qualities such as poor quality, poor architecture, low yield, or small fruit size.

The process of introgressing desirable resistance genes from non-cultivated lines into elite cultivated lines while avoiding problems with genetically linked deleterious alleles or low heritability is a long and often arduous process. In deploying alleles derived from wild relatives it is often desirable to introduce a minimal or truncated introgression that provides the desired trait but lacks detrimental effects. To aid introgression reliable marker assays are preferable to phenotypic screens. Success is furthered by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, the inventors' discovery of accurate markers associated with disease resistance will facilitate the development of tomato plants having beneficial phenotypes. For example, seed can be genotyped using the markers of the present invention to select for plants comprising desired genomic regions associated with disease resistance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding traits that are genetically tightly linked. Therefore suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among tomato species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Marker Assisted Breeding and Genetic Engineering Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita, et al. (1989) *Genomics,* 8(2), 271-278), denaturing gradient gel electrophoresis (Myers (1985) *EPO* 0273085), or cleavage fragment length polymorphisms (Life Technologies, Inc., Gaithersburg, MD), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques,* 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a tomato plant a genotype associated with disease resistance, identify a tomato plant with a genotype associated with disease resistance, and to select a tomato plant with a genotype associated with disease resistance. In certain embodiments of methods of the invention, polymorphic nucleic acids can be used to produce a tomato plant that comprises in its genome an introgressed locus associated with disease resistance. In certain embodiments of the invention, polymorphic nucleic acids can be used to breed progeny tomato plants comprising a locus or loci associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to a condition where the two alleles at a locus are different.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in tomato plants.

As used herein, nucleic acid analysis methods include, but are not limited to, PCR-based detection methods (for example, TaqMan® assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. (1986) Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to detect polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is described in U.S. Pat. Nos. 6,799,122; 6,913,879; and 6,996, 476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, CT), Agencourt Bioscience (Beverly, MA), Applied Biosystems (Foster City, CA), LI-COR Biosciences (Lincoln, NE), NimbleGen Systems (Madison, WI), Illumina (San Diego, CA), and VisiGen Biotechnologies (Houston, TX). Such nucleic acid sequencing technologies comprise formats such as parallel bead arrays, sequencing by ligation, capillary electrophoresis, electronic microchips, "biochips," microarrays, parallel microchips, and single-molecule arrays.

Some embodiments include methods for treating tomato, tomato plant parts, or the soil or substrate in which tomato plants are grown or intended to be grown with an active compound or a combination of active compounds. In some embodiments, the tomato plants are suspected of being or becoming infected with a disease, or the methods are for protecting or treating plants from fungal, viral, and bacterial infections. In some embodiments, the disease is a fungal infection, and the embodiments include methods for protecting from a fungal disease. In other embodiments, the disease comprises a fungal infection and a viral infection, and the embodiments include methods for protecting from a fungal and a viral disease. In further embodiments, the tomato plant comprises a recombinant chromosomal segment on chromosome 11 that comprises a ToCV resistance allele. In some embodiments, said chromosomal segment lacks a deleterious allele that confers a cold sensitivity trait to said plant when present. In other embodiments, said chromosomal segment comprises a Fol race 2 resistance allele that is in cis linkage with the ToCV resistance allele on chromosome 11. In further embodiments, the treatment increases tomato yield. In some embodiments, the active compound or combination of active compounds comprises a fungicidal active ingredient. In certain embodiments, the active compound is selected from the following groups: (1) inhibitors of the ergosterol synthesis, (2) inhibitors of the respiratory chain at complex I or II, (3) inhibitors of the respiratory chain at complex III, (4) inhibitors of the mitosis and cell division, (5) compounds capable of having a multisite action, (6) compounds capable of inducing a host defense, (7) inhibitors of the amino acid and/or protein biosynthesis, (8) inhibitors of the ATP production, (9) inhibitors of the cell wall synthesis, (10) inhibitors of the lipid and membrane synthesis, (11) inhibitors of the melanine biosynthesis, (12) inhibitors of the nucleic acid synthesis, (13) inhibitors of the signal transduction, (14) compounds capable of acting as uncoupler, and (15) other fungicides. Examples of such active compounds, their synthesis, and analysis are provided in European Patent Application EP3335559A1.

In some embodiments, inhibitors of the ergosterol synthesis are selected from the group consisting of (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)-cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) [2-R2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4- difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-1{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Mefentrifluconazole, and (1.082) Ipfentrifluconazole.

In some embodiments, inhibitors of the respiratory chain at complex I or II are selected from the group consisting of (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, and (2.056) N-cyclopropyl-N-(2-cyclopropylbenzyl)-3-(difluoromethyl)-5-fluoro-1-methyl-1H-pyrazole-4-carboxamide.

In some embodiments, inhibitors of the respiratory chain at complex III are selected from the group consisting of (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, and (3.029) methyl {5-[3-(2,4-dimethylphenyl)-1H-pyrazol-1-yl]-2-methylbenzyl}carbamate.

In some embodiments, inhibitors of the mitosis and cell division are selected from the group consisting of (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl) pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, and (4.025) N-(4-chloro-2,6-difluorophenyl)-4-(2-chloro-4-fluorophenyl)-1,3-dimethyl-1H-pyrazol-5-amine.

In some embodiments, compounds capable of having a multisite action are selected from the group consisting of (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper (2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, and (5.023) 6-ethyl-5,7-dioxo-6,7-dihydro-5H-pyrrolo[3',4':5,6][1,4]dithiino[2,3-c][1,2]thiazole-3-carbonitrile.

In some embodiments, compounds capable of inducing a host defense are selected from the group consisting of (6.001) acibenzolar-S-methyl, (6.002) isotianil, (6.003) probenazole, and (6.004) tiadinil.

In some embodiments, inhibitors of the amino acid and/or protein biosynthesis are selected from the group consisting of (7.001) cyprodinil, (7.002) kasugamycin, (7.003) kasugamycin hydrochloride hydrate, (7.004) oxytetracycline, (7.005) pyrimethanil, and (7.006) 3-(5-fluoro-3,3,4,4-tetramethyl-3,4-dihydroisoquinolin-1-yl)quinolone.

In some embodiments, inhibitor of the ATP production is selected from the group consisting of (8.001) silthiofam.

In some embodiments, inhibitors of the cell wall synthesis are selected from the group consisting of (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, and (9.009) (2Z)-3-(4-tert-butylphenyl)-3-(2-chloropyridin-4-yl)-1-(morpholin-4-yl)prop-2-en-1-one.

In some embodiments, inhibitors of the lipid and membrane synthesis are selected from the group consisting of (10.001) propamocarb, (10.002) propamocarb hydrochloride, and (10.003) tolclofos-methyl.

In some embodiments, inhibitors of the melanine biosynthesis are selected from the group consisting of (11.001) tricyclazole, and (11.002) 2,2,2-trifluoroethyl {3-methyl-1-[(4-methylbenzoyl)amino]butan-2-yl}carbamate.

In some embodiments, inhibitors of the nucleic acid synthesis are selected from the group consisting of (12.001) benalaxyl, (12.002) benalaxyl-M (kiralaxyl), (12.003) metalaxyl, and (12.004) metalaxyl-M (mefenoxam).

In some embodiments, inhibitors of the signal transduction are selected from the group consisting of (13.001) fludioxonil, (13.002) iprodione, (13.003) procymidone, (13.004) proquinazid, (13.005) quinoxyfen, and (13.006) vinclozolin.

In some embodiments, compounds capable of acting as uncoupler are selected from the group consisting of (14.001) fluazinam, and (14.002) meptyldinocap.

In some embodiments, other fungicides are selected from the group consisting of (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7 (2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl] ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl] ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl] ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl) quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl) oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene] amino}oxy)methyl]pyridin-2-yl}carbamate, and (15.062) 5-fluoro-4-imino-3-methyl-1-[(4-methylphenyl)sulfonyl]-3,4-dihydropyrimidin-2(1H)-one.

In certain embodiments, the active compound or combination of active compounds is selected from:
(1.001) cyproconazole, (1.002) difenoconazole, (1.003) epoxiconazole, (1.004) fenhexamid, (1.010) imazalil, (1.012) ipconazole, (1.013) metconazole, (1.017) propiconazole, (1.018) prothioconazole, (1.020) spiroxamine, (1.021) tebuconazole, (1.026) (1R,2S, 5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.059) 5-(4-chlorobenzyl)-2-(chloromethyl)-2-methyl-1-(1H-1,2,4-triazol-1-ylmethyl)cyclopentanol, (1.081) Mefentrifluconazole, and (1.082) Ipfentrifluconazole, (2.001) benzovindiflupyr, (2.002) bixafen, (2.003) boscalid, (2.005) fluopyram, (2.007) fluxapyroxad, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR, 9RS), (2.017) penflufen, (2.018) penthiopyrad, (2.019) pydiflumetofen, (2.021) sedaxane, (2.027) 3-(difluoromethyl)-1-methyl-N-(1,1,3-trimethyl-2,3-dihydro-1H-inden-4-yl)-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (3.003) azoxystrobin, (3.007) dimoxystrobin, (3.012) fluoxastrobin, (3.013) kresoxim-methyl, (3.016) picoxystrobin, (3.017) pyraclostrobin, (3.020) trifloxystrobin, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (4.005) pencycuron, (4.007) thiophanate-methyl, (4.012) 4-(2-bromo-4-fluorophenyl)-N-(2,6-difluorophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine, (5.003) captan, (5.004) chlorothalonil, (5.011) dodine, (5.012) folpet, (5.013) mancozeb,
(5.015) metiram, (5.018) propineb,
(6.002) isotianil,
(7.001) cyprodinil, (7.005) pyrimethanil,
(12.003) metalaxyl, (12.004) metalaxyl-M (mefenoxam),
(13.001) fludioxonil, (13.002) iprodione, (13.004) proquinazid, (13.005) quinoxyfen,
(14.001) fluazinam, (14.002) meptyldinocap,
(15.008) cyflufenamid, (15.010) cyprosulfamide, (15.011) flutianil, (15.012) fosetyl-aluminium, (15.016) metrafenone, (15.027) pyriofenone (chlazafenone), and (15.047) 3-(4,4-difluoro-3,3-dimethyl-3,4-dihydroisoquinolin-1-yl)quinolone, (15.048) 4-amino-5-fluoropyrimidin-2-ol (tautomeric form: 4-amino-5-fluoropyrimidin-2(1H)-one), (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.062) 5-fluoro-4-imino-3-methyl-1-[(4-methylphenyl)sulfonyl]-3,4-dihydropyrimidin-2(1H)-one.

In certain embodiments, the active compound or combination of active compounds is selected from:
- (1.002) difenoconazole, (1.010) imazalil, (1.012) ipconazole, (1.018) prothioconazole,
- (1.020) spiroxamine, (1.021) tebuconazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.059) 5-(4-chlorobenzyl)-2-(chloromethyl)-2-methyl-1-(1H-1,2,4-triazol-1-ylmethyl)cyclopentanol, (1.081) Mefentrifluconazole, and (1.082) Ipfentrifluconazole,
- (2.001) benzovindiflupyr, (2.002) bixafen, (2.005) fluopyram, (2.007) fluxapyroxad,
- (2.017) penflufen, (2.018) penthiopyrad, (2.019) pydiflumetofen, (2.021) sedaxane,
- (2.027) 3-(difluoromethyl)-1-methyl-N-(1,1,3-trimethyl-2,3-dihydro-1H-inden-4-yl)-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide,
- (3.003) azoxystrobin, (3.012) fluoxastrobin, (3.016) picoxystrobin, (3.017) pyraclostrobin, (3.020) trifloxystrobin, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide,
- (4.005) pencycuron, (4.007) thiophanate-methyl, (4.012) 4-(2-bromo-4-fluorophenyl)-N-(2,6-difluorophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine,
- (5.004) chlorothalonil, (5.011) dodine, (5.012) folpet, (5.013) mancozeb, (5.018) propineb,
- (6.002) isotianil,
- (7.005) pyrimethanil,
- (12.003) metalaxyl, (12.004) metalaxyl-M (mefenoxam),
- (13.001) fludioxonil, (13.004) proquinazid,
- (14.001) fluazinam, (14.002) meptyldinocap,
- (15.008) cyflufenamid, (15.027) pyriofenone (chlazafenone), (15.047) 3-(4,4-difluoro-3,3-dimethyl-3,4-dihydroisoquinolin-1-yl)quinolone, (15.048) 4-amino-5-fluoropyrimidin-2-ol (tautomeric form: 4-amino-5-fluoropyrimidin-2(1H)-one), (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.062) 5-fluoro-4-imino-3-methyl-1-[(4-methylphenyl)sulfonyl]-3,4-dihydropyrimidin-2(1H)-one.

In certain embodiments, the active compound or combination of active compounds is selected from:
- (1.012) ipconazole, (1.018) prothioconazole, (1.020) spiroxamine, (1.021) tebuconazole,
- (2.002) bixafen, (2.005) fluopyram, (2.017) penflufen, (2.027) 3-(difluoromethyl)-1-methyl-N-(1,1,3-trimethyl-2,3-dihydro-1H-inden-4-yl)-1H-pyrazole-4-carboxamide,
- (2.038) N-(5-chloro-2-isopropylbenzyl)-N-cyclopropyl-3-(difluoromethyl)-5-fluoro-1-methyl-1H-pyrazole-4-carboxamide,
- (3.020) trifloxystrobin, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate,
- (4.005) pencycuron,
- (5.004) chlorothalonil, (5.013) mancozeb, (5.018) propineb,
- (12.003) metalaxyl, (12.004) metalaxyl-M (mefenoxam),
- (13.001) fludioxonil, (13.004) proquinazid,
- (15.008) cyflufenamid, and (15.047) 3-(4,4-difluoro-3,3-dimethyl-3,4-dihydroisoquinolin-1-yl)quinoline.

In certain embodiments, the active compound or combination of active compounds are selected from the group (G1) consisting of the following mixtures: (I.01)+(1.001), (I.01)+(1.002), (I.01)+(1.003), (I.01)+(1.004), (I.01)+(1.005), (I.01)+(1.006), (I.01)+(1.007), (I.01)+(1.008), (I.01)+(1.009), (I.01)+(1.010), (I.01)+(1.011), (I.01)+(1.012), (I.01)+(1.013), (I.01)+(1.014), (I.01)+(1.015), (I.01)+(1.016), (I.01)+(1.017), (I.01)+(1.018), (I.01)+(1.019), (I.01)+(1.020), (I.01)+(1.021), (I.01)+(1.022), (I.01)+(1.023), (I.01)+(1.024), (I.01)+(1.025), (I.01)+(1.026), (I.01)+(1.027), (I.01)+(1.028), (I.01)+(1.029), (I.01)+(1.030), (I.01)+(1.031), (I.01)+(1.032), (I.01)+(1.033), (I.01)+(1.034), (I.01)+(1.035), (I.01)+(1.036), (I.01)+(1.037), (I.01)+(1.038), (I.01)+(1.039), (I.01)+(1.040), (I.01)+(1.041), (I.01)+(1.042), (I.01)+(1.043), (I.01)+(1.044), (I.01)+(1.045), (I.01)+(1.046), (I.01)+(1.047), (I.01)+(1.048), (I.01)+(1.049), (I.01)+(1.050), (I.01)+(1.051), (I.01)+(1.052), (I.01)+(1.053), (I.01)+(1.054), (I.01)+(1.055), (I.01)+(1.056), (I.01)+(1.057), (I.01)+(1.058), (I.01)+(1.059), (I.01)+(1.060), (I.01)+(1.061), (I.01)+(1.062), (I.01)+(1.063), (I.01)+(1.064), (I.01)+(1.065), (I.01)+(1.066), (I.01)+(1.067), (I.01)+(1.068), (I.01)+(1.069), (I.01)+(1.070), (I.01)+(1.071), (I.01)+(1.072), (I.01)+(1.073), (I.01)+(1.074), (I.01)+(1.075), (I.01)+(1.076), (I.01)+(1.077), (I.01)+(1.078), (I.01)+(1.079), (I.01)+(1.080), (I.01)+(1.081), (I.01)+(1.082), (I.01)+(2.001), (I.01)+(2.002), (I.01)+(2.003), (I.01)+(2.004), (I.01)+(2.005), (I.01)+(2.006), (I.01)+(2.007), (I.01)+(2.008), (I.01)+(2.009), (I.01)+(2.010), (I.01)+(2.011), (I.01)+(2.012), (I.01)+(2.013), (I.01)+(2.014), (I.01)+(2.015), (I.01)+(2.016), (I.01)+(2.017), (I.01)+(2.018), (I.01)+(2.019), (I.01)+(2.020), (I.01)+(2.021), (I.01)+(2.022), (I.01)+(2.023), (I.01)+(2.024), (I.01)+(2.025), (I.01)+(2.026), (I.01)+(2.027), (I.01)+(2.028), (I.01)+(2.029), (I.01)+(2.030), (I.01)+(2.031), (I.01)+(2.032), (I.01)+(2.033), (I.01)+(2.034), (I.01)+(2.035), (I.01)+(2.036), (I.01)+(2.037), (I.01)+(2.038), (I.01)+(2.039), (I.01)+(2.040), (I.01)+(2.041), (I.01)+(2.042), (I.01)+(2.043), (I.01)+(2.044), (I.01)+(2.045), (I.01)+(2.046), (I.01)+(2.047), (I.01)+(2.048), (I.01)+(2.049), (I.01)+(2.050), (I.01)+(2.051), (I.01)+(2.052), (I.01)+(2.053), (I.01)+(2.054), (I.01)+(2.055), (I.01)+(2.056), (I.01)+(3.001), (I.01)+(3.002), (I.01)+(3.003), (I.01)+(3.004), (I.01)+(3.005), (I.01)+(3.006), (I.01)+(3.007), (I.01)+(3.008), (I.01)+(3.009), (I.01)+(3.010), (I.01)+(3.011), (I.01)+(3.012), (I.01)+(3.013), (I.01)+(3.014), (I.01)+(3.015), (I.01)+(3.016), (I.01)+(3.017), (I.01)+(3.018), (I.01)+(3.019), (I.01)+(3.020), (I.01)+(3.021), (I.01)+(3.022), (I.01)+(3.023), (I.01)+(3.024), (I.01)+(3.025), (I.01)+(3.026), (I.01)+(3.027), (I.01)+(3.028), (I.01)+(3.029), (I.01)+(4.001), (I.01)+(4.002), (I.01)+(4.003), (I.01)+(4.004), (I.01)+(4.005), (I.01)+(4.006), (I.01)+(4.007), (I.01)+(4.008), (I.01)+(4.009), (I.01)+(4.010), (I.01)+(4.011), (I.01)+(4.012), (I.01)+(4.013), (I.01)+(4.014), (I.01)+(4.015), (I.01)+(4.016), (I.01)+(4.017), (I.01)+(4.018), (I.01)+(4.019), (I.01)+(4.020), (I.01)+(4.021), (I.01)+(4.022), (I.01)+(4.023), (I.01)+(4.024), (I.01)+(4.025), (I.01)+(5.001), (I.01)+(5.002), (I.01)+(5.003), (I.01)+(5.004), (I.01)+(5.005), (I.01)+(5.006), (I.01)+(5.007), (I.01)+(5.008), (I.01)+(5.009), (I.01)+(5.010), (I.01)+(5.011), (I.01)+(5.012), (I.01)+(5.013), (I.01)+(5.014), (I.01)+(5.015), (I.01)+(5.016), (I.01)+(5.017), (I.01)+(5.018), (I.01)+(5.019), (I.01)+(5.020), (I.01)+(5.021), (I.01)+(5.022), (I.01)+(5.023), (I.01)+(6.001), (I.01)+(6.002), (I.01)+(6.003), (I.01)+(6.004), (I.01)+(7.001), (I.01)+(7.002), (I.01)+(7.003), (I.01)+(7.004), (I.01)+(7.005), (I.01)+(7.006), (I.01)+(8.001), (I.01)+(9.001), (I.01)+(9.002), (I.01)+(9.003), (I.01)+(9.004), (I.01)+(9.005), (I.01)+(9.006), (I.01)+(9.007), (I.01)+(9.008), (I.01)+(9.009), (I.01)+(10.001), (I.01)+(10.002), (I.01)+(10.003), (I.01)+(11.001), (I.01)+(11.002), (I.01)+(12.001), (I.01)+(12.002), (I.01)+(12.003), (I.01)+(12.004), (I.01)+(13.001), (I.01)+(13.002), (I.01)+(13.003), (I.01)+(13.004), (I.01)+(13.005), (I.01)+(13.006), (I.01)+(14.001), (I.01)+(14.002), (I.01)+(15.001), (I.01)+(15.002), (I.01)+(15.003), (I.01)+(15.004), (I.01)+(15.005), (I.01)+(15.006), (I.01)+(15.007), (I.01)+(15.008), (I.01)+(15.009), (I.01)+(15.010), (I.01)+(15.011), (I.01)+(15.012), (I.01)+(15.013), (I.01)+(15.014), (I.01)+(15.015), (I.01)+(15.016), (I.01)+(15.017), (I.01)+(15.018), (I.01)+(15.019), (I.01)+(15.020), (I.01)+(15.021), (I.01)+(15.022), (I.01)+(15.023), (I.01)+(15.024), (I.01)+(15.025), (I.01)+(15.026), (I.01)+(15.027), (I.01)+(15.028), (I.01)+(15.029), (I.01)+(15.030), (I.01)+(15.031), (I.01)+(15.032), (I.01)+(15.033), (I.01)+(15.034), (I.01)+(15.035), (I.01)+(15.036), (I.01)+(15.037), (I.01)+(15.038), (I.01)+(15.039), (I.01)+(15.040), (I.01)+(15.041), (I.01)+(15.042), (I.01)+(15.043), (I.01)+(15.044), (I.01)+(15.045), (I.01)+(15.046), (I.01)+(15.047), (I.01)+(15.048), (I.01)+(15.049), (I.01)+(15.050), (I.01)+(15.051), (I.01)+(15.052), (I.01)+(15.053), (I.01)+(15.054), (I.01)+(15.055), (I.01)+(15.056), (I.01)+(15.057), (I.01)+(15.058), (I.01)+(15.059), (I.01)+(15.060), (I.01)+(15.061), and (I.01)+(15.062).

In certain embodiments, the active compound or combination of active compounds are selected from the group (G2) consisting of the following mixtures: (I.59)+(1.001), (I.59)+(1.002), (I.59)+(1.003), (I.59)+(1.004), (I.59)+(1.005), (I.59)+(1.006), (I.59)+(1.007), (I.59)+(1.008), (I.59)+(1.009), (I.59)+(1.010), (I.59)+(1.011), (I.59)+(1.012), (I.59)+(1.013), (I.59)+(1.014), (I.59)+(1.015), (I.59)+(1.016), (I.59)+(1.017), (I.59)+(1.018), (I.59)+(1.019), (I.59)+(1.020), (I.59)+(1.021), (I.59)+(1.022), (I.59)+(1.023), (I.59)+(1.024), (I.59)+(1.025), (I.59)+(1.026), (I.59)+(1.027), (I.59)+(1.028), (I.59)+(1.029), (I.59)+(1.030), (I.59)+(1.031), (I.59)+(1.032), (I.59)+(1.033), (I.59)+(1.034), (I.59)+(1.035), (I.59)+(1.036), (I.59)+(1.037), (I.59)+(1.038), (I.59)+(1.039), (I.59)+(1.040), (I.59)+(1.041), (I.59)+(1.042), (I.59)+(1.043), (I.59)+(1.044), (I.59)+(1.045), (I.59)+(1.046), (I.59)+(1.047), (I.59)+(1.048), (I.59)+(1.049), (I.59)+(1.050), (I.59)+(1.051), (I.59)+(1.052), (I.59)+(1.053), (I.59)+(1.054), (I.59)+(1.055), (I.59)+(1.056), (I.59)+(1.057), (I.59)+(1.058), (I.59)+(1.059), (I.59)+(1.060), (I.59)+(1.061), (I.59)+(1.062), (I.59)+(1.063), (I.59)+(1.064), (I.59)+(1.065), (I.59)+(1.066), (I.59)+(1.067), (I.59)+(1.068), (I.59)+(1.069), (I.59)+(1.070), (I.59)+(1.071), (I.59)+(1.072), (I.59)+(1.073), (I.59)+(1.074), (I.59)+(1.075), (I.59)+(1.076), (I.59)+(1.077), (I.59)+(1.078), (I.59)+(1.079), (I.59)+(1.080), (I.59)+(1.081), (I.59)+(1.082), (I.59)+(2.001), (I.59)+(2.002), (I.59)+(2.003), (I.59)+(2.004), (I.59)+(2.005), (I.59)+(2.006), (I.59)+(2.007), (I.59)+(2.008), (I.59)+(2.009), (I.59)+(2.010), (I.59)+(2.011), (I.59)+(2.012), (I.59)+(2.013), (I.59)+(2.014), (I.59)+(2.015), (I.59)+(2.016), (I.59)+(2.017), (I.59)+(2.018), (I.59)+(2.019), (I.59)+(2.020), (I.59)+(2.021), (I.59)+(2.022), (I.59)+(2.023), (I.59)+(2.024), (I.59)+(2.025), (I.59)+(2.026), (I.59)+(2.027), (I.59)+(2.028), (I.59)+(2.029), (I.59)+(2.030), (I.59)+(2.031), (I.59)+(2.032), (I.59)+(2.033), (I.59)+(2.034), (I.59)+(2.035), (I.59)+(2.036), (I.59)+(2.037), (I.59)+(2.038), (I.59)+(2.039), (I.59)+(2.040), (I.59)+(2.041), (I.59)+(2.042), (I.59)+(2.043), (I.59)+(2.044), (I.59)+(2.045), (I.59)+(2.046), (I.59)+(2.047), (I.59)+(2.048), (I.59)+(2.049), (I.59)+(2.050), (I.59)+(2.051), (I.59)+(2.052), (I.59)+(2.053), (I.59)+(2.054), (I.59)+(2.055), (I.59)+(2.056), (I.59)+(3.001), (I.59)+(3.002), (I.59)+(3.003), (I.59)+(3.004), (I.59)+(3.005), (I.59)+(3.006), (I.59)+(3.007), (I.59)+(3.008), (I.59)+(3.009), (I.59)+(3.010), (I.59)+(3.011), (I.59)+(3.012), (I.59)+(3.013), (I.59)+(3.014), (I.59)+(3.015), (I.59)+(3.016), (I.59)+(3.017), (I.59)+(3.018), (I.59)+(3.019), (I.59)+(3.020), (I.59)+(3.021), (I.59)+(3.022), (I.59)+(3.023), (I.59)+(3.024), (I.59)+(3.025), (I.59)+(3.026), (I.59)+(3.027), (I.59)+(3.028), (I.59)+(3.029), (I.59)+(4.001), (I.59)+(4.002), (I.59)+(4.003), (I.59)+(4.004), (I.59)+(4.005), (I.59)+(4.006), (I.59)+(4.007), (I.59)+(4.008), (I.59)+(4.009), (I.59)+(4.010), (I.59)+(4.011), (I.59)+(4.012), (I.59)+(4.013), (I.59)+(4.014), (I.59)+(4.015), (I.59)+(4.016), (I.59)+(4.017), (I.59)+(4.018), (I.59)+(4.019), (I.59)+(4.020), (I.59)+(4.021), (I.59)+(4.022), (I.59)+(4.023), (I.59)+(4.024), (I.59)+(4.025), (I.59)+(5.001), (I.59)+(5.002), (I.59)+(5.003), (I.59)+(5.004), (I.59)+(5.005), (I.59)+(5.006), (I.59)+(5.007), (I.59)+(5.008), (I.59)+(5.009), (I.59)+(5.010), (I.59)+(5.011), (I.59)+(5.012), (I.59)+(5.013), (I.59)+(5.014), (I.59)+(5.015), (I.59)+(5.016), (I.59)+(5.017), (I.59)+(5.018), (I.59)+(5.019), (I.59)+(5.020), (I.59)+(5.021), (I.59)+(5.022), (I.59)+(5.023), (I.59)+(6.001), (I.59)+(6.002), (I.59)+(6.003), (I.59)+(6.004), (I.59)+(7.001), (I.59)+(7.002), (I.59)+(7.003), (I.59)+(7.004), (I.59)+(7.005), (I.59)+(7.006), (I.59)+(8.001), (I.59)+(9.001), (I.59)+(9.002), (I.59)+(9.003), (I.59)+(9.004), (I.59)+(9.005), (I.59)+(9.006), (I.59)+(9.007), (I.59)+(9.008), (I.59)+(9.009), (I.59)+(10.001), (I.59)+(10.002), (I.59)+(10.003), (I.59)+(11.001), (I.59)+(11.002), (I.59)+(12.001), (I.59)+(12.002), (I.59)+(12.003), (I.59)+(12.004), (I.59)+(13.001), (I.59)+(13.002), (I.59)+(13.003), (I.59)+(13.004), (I.59)+(13.005), (I.59)+(13.006), (I.59)+(14.001), (I.59)+(14.002), (I.59)+(15.001), (I.59)+(15.002), (I.59)+(15.003), (I.59)+(15.004), (I.59)+(15.005), (I.59)+(15.006), (I.59)+(15.007), (I.59)+(15.008), (I.59)+(15.009), (I.59)+(15.010), (I.59)+(15.011), (I.59)+(15.012), (I.59)+(15.013), (I.59)+(15.014), (I.59)+(15.015), (I.59)+(15.016), (I.59)+(15.017), (I.59)+(15.018), (I.59)+(15.019), (I.59)+(15.020), (I.59)+(15.021), (I.59)+(15.022), (I.59)+(15.023), (I.59)+(15.024), (I.59)+(15.025), (I.59)+(15.026), (I.59)+(15.027), (I.59)+(15.028), (I.59)+(15.029), (I.59)+(15.030), (I.59)+(15.031), (I.59)+(15.032), (I.59)+(15.033), (I.59)+(15.034), (I.59)+(15.035), (I.59)+(15.036), (I.59)+(15.037), (I.59)+(15.038), (I.59)+(15.039), (I.59)+(15.040), (I.59)+(15.041), (I.59)+(15.042), (I.59)+(15.043), (I.59)+(15.044), (I.59)+(15.045), (I.59)+(15.046), (I.59)+(15.047), (I.59)+(15.048), (I.59)+(15.049), (I.59)+(15.050), (I.59)+(15.051), (I.59)+(15.052), (I.59)+(15.053), (I.59)+(15.054), (I.59)+(15.055), (I.59)+(15.056), (I.59)+(15.057), (I.59)+(15.058), (I.59)+(15.059), (I.59)+(15.060), (I.59)+(15.061), and (I.59)+(15.062).

In certain embodiments, the active compound or combination of active compounds are selected from the group (G3) consisting of the following mixtures: (I.81)+(1.001), (I.81)+(1.002), (I.81)+(1.003), (I.81)+(1.004), (I.81)+(1.005), (I.81)+(1.006), (I.81)+(1.007), (I.81)+(1.008), (I.81)+(1.009), (I.81)+(1.010), (I.81)+(1.011), (I.81)+(1.012), (I.81)+(1.013), (I.81)+(1.014), (I.81)+(1.015), (I.81)+(1.016), (I.81)+(1.017), (I.81)+(1.018), (I.81)+(1.019), (I.81)+(1.020), (I.81)+(1.021), (I.81)+(1.022), (I.81)+(1.023), (I.81)+(1.024), (I.81)+(1.025), (I.81)+(1.026), (I.81)+(1.027), (I.81)+(1.028), (I.81)+(1.029), (I.81)+(1.030), (I.81)+(1.031), (I.81)+(1.032), (I.81)+(1.033), (I.81)+(1.034), (I.81)+(1.035), (I.81)+(1.036), (I.81)+(1.037), (I.81)+(1.038), (I.81)+(1.039), (I.81)+(1.040), (I.81)+(1.041), (I.81)+(1.042), (I.81)+(1.043), (I.81)+(1.044), (I.81)+(1.045), (I.81)+(1.046), (I.81)+(1.047), (I.81)+(1.048), (I.81)+(1.049), (I.81)+(1.050), (I.81)+(1.051), (I.81)+(1.052), (I.81)+(1.053), (I.81)+(1.054), (I.81)+(1.055), (I.81)+(1.056), (I.81)+(1.057), (I.81)+(1.058), (I.81)+(1.059), (I.81)+(1.060), (I.81)+(1.061), (I.81)+(1.062), (I.81)+(1.063), (I.81)+(1.064), (I.81)+(1.065), (I.81)+(1.066), (I.81)+(1.067), (I.81)+(1.068), (I.81)+(1.069), (I.81)+(1.070), (I.81)+(1.071), (I.81)+(1.072), (I.81)+(1.073), (I.81)+(1.074), (I.81)+(1.075), (I.81)+(1.076), (I.81)+(1.077), (I.81)+(1.078), (I.81)+(1.079), (I.81)+(1.080), (I.81)+(1.081), (I.81)+(1.082), (I.81)+(2.001), (I.81)+(2.002), (I.81)+(2.003), (I.81)+(2.004), (I.81)+(2.005), (I.81)+(2.006), (I.81)+(2.007), (I.81)+(2.008), (I.81)+(2.009), (I.81)+(2.010), (I.81)+(2.011), (I.81)+(2.012), (I.81)+(2.013), (I.81)+(2.014), (I.81)+(2.015), (I.81)+(2.016), (I.81)+(2.017), (I.81)+(2.018), (I.81)+(2.019), (I.81)+(2.020), (I.81)+(2.021), (I.81)+(2.022), (I.81)+(2.023), (I.81)+(2.024), (I.81)+(2.025), (I.81)+(2.026), (I.81)+(2.027), (I.81)+(2.028), (I.81)+(2.029), (I.81)+(2.030), (I.81)+(2.031), (I.81)+(2.032), (I.81)+(2.033), (I.81)+(2.034), (I.81)+(2.035), (I.81)+(2.036), (I.81)+(2.037), (I.81)+(2.038), (I.81)+(2.039), (I.81)+(2.040), (I.81)+(2.041), (I.81)+(2.042), (I.81)+(2.043), (I.81)+(2.044), (I.81)+(2.045), (I.81)+(2.046), (I.81)+(2.047), (I.81)+(2.048), (I.81)+(2.049), (I.81)+(2.050), (I.81)+(2.051), (I.81)+(2.052), (I.81)+(2.053), (I.81)+(2.054), (I.81)+(2.055), (I.81)+(2.056), (I.81)+(3.001), (I.81)+(3.002), (I.81)+(3.003), (I.81)+(3.004), (I.81)+(3.005), (I.81)+(3.006), (I.81)+(3.007), (I.81)+(3.008), (I.81)+(3.009), (I.81)+(3.010), (I.81)+(3.011), (I.81)+(3.012), (I.81)+(3.013), (I.81)+(3.014), (I.81)+(3.015), (I.81)+(3.016), (I.81)+(3.017), (I.81)+(3.018), (I.81)+(3.019), (I.81)+(3.020), (I.81)+(3.021), (I.81)+(3.022), (I.81)+(3.023), (I.81)+(3.024), (I.81)+(3.025), (I.81)+(3.026), (I.81)+(3.027), (I.81)+(3.028), (I.81)+(3.029), (I.81)+(4.001), (I.81)+(4.002), (I.81)+(4.003), (I.81)+(4.004), (I.81)+(4.005), (I.81)+(4.006), (I.81)+(4.007), (I.81)+(4.008), (I.81)+(4.009), (I.81)+(4.010), (I.81)+(4.011), (I.81)+(4.012), (I.81)+(4.013), (I.81)+(4.014), (I.81)+(4.015), (I.81)+(4.016), (I.81)+(4.017), (I.81)+(4.018), (I.81)+(4.019), (I.81)+(4.020), (I.81)+(4.021), (I.81)+(4.022), (I.81)+(4.023), (I.81)+(4.024), (I.81)+(4.025), (I.81)+(5.001), (I.81)+(5.002), (I.81)+(5.003), (I.81)+(5.004), (I.81)+(5.005), (I.81)+(5.006), (I.81)+(5.007), (I.81)+(5.008), (I.81)+(5.009), (I.81)+(5.010), (I.81)+(5.011), (I.81)+(5.012), (I.81)+(5.013), (I.81)+(5.014), (I.81)+(5.015), (I.81)+(5.016), (I.81)+(5.017), (I.81)+(5.018), (I.81)+(5.019), (I.81)+(5.020), (I.81)+(5.021), (I.81)+(5.022), (I.81)+(5.023), (I.81)+(6.001), (I.81)+(6.002), (I.81)+(6.003), (I.81)+(6.004), (I.81)+(7.001), (I.81)+(7.002), (I.81)+(7.003), (I.81)+(7.004), (I.81)+(7.005), (I.81)+(7.006), (I.81)+(8.001), (I.81)+(9.001), (I.81)+(9.002), (I.81)+(9.003), (I.81)+(9.004), (I.81)+(9.005), (I.81)+(9.006), (I.81)+(9.007), (I.81)+(9.008), (I.81)+(9.009), (I.81)+(10.001), (I.81)+(10.002), (I.81)+(10.003), (I.81)+(11.001), (I.81)+(11.002), (I.81)+(12.001), (I.81)+(12.002), (I.81)+(12.003), (I.81)+(12.004), (I.81)+(13.001), (I.81)+(13.002), (I.81)+(13.003), (I.81)+(13.004), (I.81)+(13.005), (I.81)+(13.006), (I.81)+(14.001), (I.81)+(14.002), (I.81)+(15.001), (I.81)+(15.002), (I.81)+(15.003), (I.81)+(15.004), (I.81)+(15.005), (I.81)+(15.006), (I.81)+(15.007), (I.81)+(15.008), (I.81)+(15.009), (I.81)+(15.010), (I.81)+(15.011), (I.81)+(15.012), (I.81)+(15.013), (I.81)+(15.014), (I.81)+(15.015), (I.81)+(15.016), (I.81)+(15.017), (I.81)+(15.018), (I.81)+(15.019), (I.81)+(15.020), (I.81)+(15.021), (I.81)+(15.022), (I.81)+(15.023), (I.81)+(15.024), (I.81)+(15.025), (I.81)+(15.026), (I.81)+(15.027), (I.81)+(15.028), (I.81)+(15.029), (I.81)+(15.030), (I.81)+(15.031), (I.81)+(15.032), (I.81)+(15.033), (I.81)+(15.034), (I.81)+(15.035), (I.81)+(15.036), (I.81)+(15.037), (I.81)+(15.038), (I.81)+(15.039), (I.81)+(15.040), (I.81)+(15.041), (I.81)+(15.042), (I.81)+(15.043), (I.81)+(15.044), (I.81)+(15.045), (I.81)+(15.046), (I.81)+(15.047), (I.81)+(15.048), (I.81)+(15.049), (I.81)+(15.050), (I.81)+(15.051), (I.81)+(15.052), (I.81)+(15.053), (I.81)+(15.054), (I.81)+(15.055), (I.81)+(15.056), (I.81)+(15.057), (I.81)+(15.058), (I.81)+(15.059), (I.81)+(15.060), (I.81)+(15.061), and (I.81)+(15.062).

In certain embodiments, the active compound or combination of active compounds are selected from the group (G4) consisting of the following mixtures: (I.91)+(1.001), (I.91)+(1.002), (I.91)+(1.003), (I.91)+(1.004), (I.91)+(1.005), (I.91)+(1.006), (I.91)+(1.007), (I.91)+(1.008), (I.91)+(1.009), (I.91)+(1.010), (I.91)+(1.011), (I.91)+(1.012), (I.91)+(1.013), (I.91)+(1.014), (I.91)+(1.015), (I.91)+(1.016), (I.91)+(1.017), (I.91)+(1.018), (I.91)+(1.019), (I.91)+(1.020), (I.91)+(1.021), (I.91)+(1.022), (I.91)+(1.023), (I.91)+(1.024), (I.91)+(1.025), (I.91)+(1.026), (I.91)+(1.027), (I.91)+(1.028), (I.91)+(1.029), (I.91)+(1.030), (I.91)+(1.031), (I.91)+(1.032), (I.91)+(1.033), (I.91)+(1.034), (I.91)+(1.035), (I.91)+(1.036), (I.91)+(1.037), (I.91)+(1.038), (I.91)+(1.039), (I.91)+(1.040), (I.91)+(1.041), (I.91)+(1.042), (I.91)+(1.043), (I.91)+(1.044), (I.91)+(1.045), (I.91)+(1.046), (I.91)+(1.047), (I.91)+(1.048), (I.91)+(1.049), (I.91)+(1.050), (I.91)+(1.051), (I.91)+(1.052), (I.91)+(1.053), (I.91)+(1.054), (I.91)+(1.055), (I.91)+(1.056), (I.91)+(1.057), (I.91)+(1.058), (I.91)+(1.059), (I.91)+(1.060), (I.91)+(1.061), (I.91)+(1.062), (I.91)+(1.063), (I.91)+(1.064), (I.91)+(1.065), (I.91)+(1.066), (I.91)+(1.067), (I.91)+(1.068), (I.91)+(1.069), (I.91)+(1.070), (I.91)+(1.071), (I.91)+(1.072), (I.91)+(1.073), (I.91)+(1.074), (I.91)+(1.075), (I.91)+(1.076), (I.91)+(1.077), (I.91)+(1.078), (I.91)+(1.079), (I.91)+(1.080), (I.91)+(1.081), (I.91)+(1.082), (I.91)+(2.001), (I.91)+(2.002), (I.91)+(2.003), (I.91)+(2.004), (I.91)+(2.005), (I.91)+(2.006), (I.91)+(2.007), (I.91)+(2.008), (I.91)+(2.009), (I.91)+(2.010), (I.91)+(2.011), (I.91)+(2.012), (I.91)+(2.013), (I.91)+(2.014), (I.91)+(2.015), (I.91)+(2.016), (I.91)+(2.017), (I.91)+(2.018), (I.91)+(2.019), (I.91)+(2.020), (I.91)+(2.021), (I.91)+(2.022), (I.91)+(2.023), (I.91)+(2.024), (I.91)+(2.025), (I.91)+(2.026), (I.91)+(2.027), (I.91)+(2.028), (I.91)+(2.029), (I.91)+(2.030), (I.91)+(2.031), (I.91)+(2.032), (I.91)+(2.033), (I.91)+(2.034), (I.91)+(2.035), (I.91)+(2.036), (I.91)+(2.037), (I.91)+(2.038), (I.91)+(2.039), (I.91)+(2.040), (I.91)+(2.041), (I.91)+(2.042), (I.91)+(2.043), (I.91)+(2.044), (I.91)+(2.045), (I.91)+(2.046), (I.91)+(2.047), (I.91)+(2.048), (I.91)+(2.049), (I.91)+(2.050), (I.91)+(2.051), (I.91)+(2.052), (I.91)+(2.053), (I.91)+(2.054), (I.91)+(2.055), (I.91)+(2.056), (I.91)+(3.001), (I.91)+(3.002), (I.91)+(3.003), (I.91)+(3.004), (I.91)+(3.005), (I.91)+(3.006), (I.91)+(3.007), (I.91)+(3.008), (I.91)+(3.009), (I.91)+(3.010), (I.91)+

(3.011), (I.91)+(3.012), (I.91)+(3.013), (I.91)+(3.014), (I.91)+(3.015), (I.91)+(3.016), (I.91)+(3.017), (I.91)+(3.018), (I.91)+(3.019), (I.91)+(3.020), (I.91)+(3.021), (I.91)+(3.022), (I.91)+(3.023), (I.91)+(3.024), (I.91)+(3.025), (I.91)+(3.026), (I.91)+(3.027), (I.91)+(3.028), (I.91)+(3.029), (I.91)+(4.001), (I.91)+(4.002), (I.91)+(4.003), (I.91)+(4.004), (I.91)+(4.005), (I.91)+(4.006), (I.91)+(4.007), (I.91)+(4.008), (I.91)+(4.009), (I.91)+(4.010), (I.91)+(4.011), (I.91)+(4.012), (I.91)+(4.013), (I.91)+(4.014), (I.91)+(4.015), (I.91)+(4.016), (I.91)+(4.017), (I.91)+(4.018), (I.91)+(4.019), (I.91)+(4.020), (I.91)+(4.021), (I.91)+(4.022), (I.91)+(4.023), (I.91)+(4.024), (I.91)+(4.025), (I.91)+(5.001), (I.91)+(5.002), (I.91)+(5.003), (I.91)+(5.004), (I.91)+(5.005), (I.91)+(5.006), (I.91)+(5.007), (I.91)+(5.008), (I.91)+(5.009), (I.91)+(5.010), (I.91)+(5.011), (I.91)+(5.012), (I.91)+(5.013), (I.91)+(5.014), (I.91)+(5.015), (I.91)+(5.016), (I.91)+(5.017), (I.91)+(5.018), (I.91)+(5.019), (I.91)+(5.020), (I.91)+(5.021), (I.91)+(5.022), (I.91)+(5.023), (I.91)+(6.001), (I.91)+(6.002), (I.91)+(6.003), (I.91)+(6.004), (I.91)+(7.001), (I.91)+(7.002), (I.91)+(7.003), (I.91)+(7.004), (I.91)+(7.005), (I.91)+(7.006), (I.91)+(8.001), (I.91)+(9.001), (I.91)+(9.002), (I.91)+(9.003), (I.91)+(9.004), (I.91)+(9.005), (I.91)+(9.006), (I.91)+(9.007), (I.91)+(9.008), (I.91)+(9.009), (I.91)+(10.001), (I.91)+(10.002), (I.91)+(10.003), (I.91)+(11.001), (I.91)+(11.002), (I.91)+(12.001), (I.91)+(12.002), (I.91)+(12.003), (I.91)+(12.004), (I.91)+(13.001), (I.91)+(13.002), (I.91)+(13.003), (I.91)+(13.004), (I.91)+(13.005), (I.91)+(13.006), (I.91)+(14.001), (I.91)+(14.002), (I.91)+(15.001), (I.91)+(15.002), (I.91)+(15.003), (I.91)+(15.004), (I.91)+(15.005), (I.91)+(15.006), (I.91)+(15.007), (I.91)+(15.008), (I.91)+(15.009), (I.91)+(15.010), (I.91)+(15.011), (I.91)+(15.012), (I.91)+(15.013), (I.91)+(15.014), (I.91)+(15.015), (I.91)+(15.016), (I.91)+(15.017), (I.91)+(15.018), (I.91)+(15.019), (I.91)+(15.020), (I.91)+(15.021), (I.91)+(15.022), (I.91)+(15.023), (I.91)+(15.024), (I.91)+(15.025), (I.91)+(15.026), (I.91)+(15.027), (I.91)+(15.028), (I.91)+(15.029), (I.91)+(15.030), (I.91)+(15.031), (I.91)+(15.032), (I.91)+(15.033), (I.91)+(15.034), (I.91)+(15.035), (I.91)+(15.036), (I.91)+(15.037), (I.91)+(15.038), (I.91)+(15.039), (I.91)+(15.040), (I.91)+(15.041), (I.91)+(15.042), (I.91)+(15.043), (I.91)+(15.044), (I.91)+(15.045), (I.91)+(15.046), (I.91)+(15.047), (I.91)+(15.048), (I.91)+(15.049), (I.91)+(15.050), (I.91)+(15.051), (I.91)+(15.052), (I.91)+(15.053), (I.91)+(15.054), (I.91)+(15.055), (I.91)+(15.056), (I.91)+(15.057), (I.91)+(15.058), (I.91)+(15.059), (I.91)+(15.060), (I.91)+(15.061), and (I.91)+(15.062).

In certain embodiments, the active compound or combination of active compounds are selected from the mixtures belonging to group (G1) or (G2).

In certain embodiments, the active compound or combination of active compounds are selected from the group (G1-A) consisting of the following mixtures: (I.01)+(1.012), (I.01)+(1.018), (I.01)+(1.020), (I.01)+(1.021), (I.01)+(2.002), (I.01)+(2.005), (I.01)+(2.017), (I.01)+(2.027), (I.01)+(2.038), (I.01)+(3.020), (I.01)+(3.025), (I.01)+(4.005), (I.01)+(5.004), (I.01)+(5.013), (I.01)+(5.018), (I.01)+(12.003), (I.01)+(12.004), (I.01)+(13.001), (I.01)+(13.004), (I.01)+(15.008), (I.01)+(15.047).

In certain embodiments, the active compound or combination of active compounds are selected from the group (G2-A) consisting of the following mixtures: (I.59)+(1.012), (I.59)+(1.018), (I.59)+(1.020), (I.59)+(1.021), (I.59)+(2.002), (I.59)+(2.005), (I.59)+(2.017), (I.59)+(2.027), (I.59)+(2.038), (I.59)+(3.020), (I.59)+(3.025), (I.59)+(4.005), (I.59)+(5.004), (I.59)+(5.013), (I.59)+(5.018), (I.59)+(12.003), (I.59)+(12.004), (I.59)+(13.001), (I.59)+(13.004), (I.59)+(15.008), (I.59)+(15.047).

In certain embodiments, the active compound or combination of active compounds are selected from the group (G3-A) consisting of the following mixtures: (I.81)+(1.012), (I.81)+(1.018), (I.81)+(1.020), (I.81)+(1.021), (I.81)+(2.002), (I.81)+(2.005), (I.81)+(2.017), (I.81)+(2.027), (I.81)+(2.038), (I.81)+(3.020), (I.81)+(3.025), (I.81)+(4.005), (I.81)+(5.004), (I.81)+(5.013), (I.81)+(5.018), (I.81)+(12.003), (I.81)+(12.004), (I.81)+(13.001), (I.81)+(13.004), (I.81)+(15.008), (I.81)+(15.047).

In certain embodiments, the active compound or combination of active compounds are selected from the group (G4-A) consisting of the following mixtures: (I.91)+(1.012), (I.91)+(1.018), (I.91)+(1.020), (I.91)+(1.021), (I.91)+(2.002), (I.91)+(2.005), (I.91)+(2.017), (I.91)+(2.027), (I.91)+(2.038), (I.91)+(3.020), (I.91)+(3.025), (I.91)+(4.005), (I.91)+(5.004), (I.91)+(5.013), (I.91)+(5.018), (I.91)+(12.003), (I.91)+(12.004), (I.91)+(13.001), (I.91)+(13.004), (I.91)+(15.008), (I.91)+(15.047).

In certain embodiments, the active compound or combination of active compounds are selected from the mixtures belonging to group (G1-A) or (G2-A).

In certain embodiments, the active compound or combination of active compounds can be present in a broad range of effective weight ratio of A:B, for example in a range of 100:1 to 1:100, preferably in a weight ratio of 50:1 to 1:50, most preferably in a weight ratio of 20:1 to 1:20. Further ratios of A:B which can be used according to the present invention with increasing preference in the order given are: 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Where a compound (A) or a compound (B) can be present in isomeric forms and/or tautomeric forms, such a compound is understood herein above and herein below also to include, where applicable, corresponding isomeric and/or tautomeric forms or mixtures thereof, even when these are not specifically mentioned in each case.

Various genetic engineering technologies have been developed and may be used by those of skill in the art to introduce traits in plants. In certain aspects of the claimed invention, traits are introduced into tomato plants via altering or introducing a single genetic locus or transgene into the genome of a variety or progenitor thereof. Methods of genetic engineering to modify, delete, or insert genes and polynucleotides into the genomic DNA of plants are well-known in the art.

In specific embodiments of the invention, improved tomato lines can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a tomato plant genome (see, for example Sauer et al., *Plant Physiol,* 170(4): 1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the invention or may, alternatively, be used for the preparation of transgenes which can be introduced by backcrossing. Methods for the transformation of plants that are well-known to those of skill in the art and applicable to many crop species include, but are not limited to, electroporation, microprojectile bombardment, *Agrobacterium*-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Nat. Biotechnol.,* 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.,* 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, for example, Potrykus et al., *Mol. Gen. Genet.,* 199:183-188, 1985; Omirulleh et al., *Plant Mol. Biol.,* 21(3):415-428, 1993; Fromm et al., *Nature,* 312:791-793, 1986; Uchimiya et al., *Mol. Gen. Genet.,* 204:204, 1986; Marcotte et al., *Nature,* 335:454, 1988). Transformation of plants and expression of foreign genetic elements is exemplified in Choi et al. (*Plant Cell Rep.,* 13:344-348, 1994), and Ellul et al. (*Theor. Appl. Genet.,* 107:462-469, 2003).

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which tomato plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of tomato breeding. An "elite population" is an assortment of elite individuals or varieties that can be used to represent the state of the art in terms of agronomically superior genotypes of a given crop species, such as tomato. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "tolerance locus" means a locus associated with tolerance or resistance to disease. For instance, a tolerance locus according to the present invention may, in one embodiment, control tolerance or susceptibility to ToCV and/or Fol race 2.

As used herein, "tolerance" or "improved tolerance" in a plant refers to the ability of the plant to perform well, for example by maintaining yield, under disease conditions. Tolerance may also refer to the ability of a plant to maintain a plant vigor phenotype under disease conditions. Tolerance is a relative term, indicating that a "tolerant" plant is more able to maintain performance compared to a different (less tolerant) plant (e.g. a different plant variety) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance of different plants, plant varieties, or plant families under disease conditions, and furthermore, will also recognize the phenotypic gradations of "tolerance."

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

As used herein, "resistance allele" means the nucleic acid sequence associated with tolerance or resistance to disease.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. Deposit Information

A deposit of tomato line CHI-1120-0340, which contains the recombination event described herein, has been made with the Provasoli-Guillard National Center for Marine Algae and Microbiota (NCMA), 60 Bigelow Drive, East Boothbay, Maine, 04544, USA. The date of deposit for tomato line CHI-1120-0340 is Jul. 7, 2020. The accession number for the deposited seeds of tomato line CHI-1120-0340 is NCMA Accession Number 202007005. Upon issuance of a patent, all restrictions upon the deposit will be removed, and the deposit is intended to meet all of the requirements of 37 C.F.R. §§ 1.801-1.809. The deposit has been accepted under the Budapest Treaty will be maintained in the depository for a period of 30 years, 5 years after the last request, or the effective life of the patent, whichever is longer, and will be replaced if necessary during that period.

EXAMPLES

Example 1. *Fusarium oxysporum* f. Sp. *Lycopersici* Race 2 Resistance Assays

*Fusarium* wilt resistance can be measured using the assay described here. Inoculum is prepared by adding Fol race 2 culture from storage to 500 ml sterile Czapek-Dox broth (containing per liter: 30 g sucrose, 3 g sodium nitrate, 1 g dipotassium phosphate, 0.5 g magnesium sulphate, 0.5 g potassium chloride, and 0.01 g ferrous sulphate, with a final pH of 7.3). The culture is maintained at 25° C. in an orbital shaker at 30 rpm for 5-7 days. The final suspension should be diluted with water to a concentration of $1*10^6$ spores/ml.

The experiment should contain between 20-60 plants per genotype and include a Fol race 2 sensitive and Fol race 2 resistant control. The sensitive control is ideally a variety that does not contain resistance genes against any of the Fol races (e.g. tomato variety 'Glamour'). The resistant control should be a variety that contains the I-2 locus and has high resistance against Fol race 2 (e.g. tomato variety 'Tradiro').

Plants are germinated in a substrate that allows easy removal of the seedlings for inoculation of the roots, such as moist vermiculite. Seed are germinated and when the cotyledons are totally expanded and the first leaf starts to develop the seedlings are ready for inoculation, which is generally about 10 days after sowing. Prior to inoculation, it should be ensured that the plants are turgid and that the inoculum is at room temperature. Pour some inoculum in a small plastic container. The small plants should be taken out of their pots and their roots immersed in the inoculum for 2 minutes. Less than half the roots should be immersed to avoid plant death during inoculation. The plants should next be transplanted to a standard growth environment where the substrate is not too wet. After transplanting, plants are kept in the shade for at least 1-2 days and protected from direct sunlight. In the darker winter months, LED light can be used to supplement light needs of the plants. It may also be necessary to slightly heat the soil to ensure fungal growth. Plants are grown at 25° C./17° C. day/night cycle for 10-12 days. The experiment is evaluated 3-4 weeks after inoculation. The following rating scale can be used during evaluation: 1=healthy plants with no external symptoms; 3=stunted growth, i.e. reduced plant height compared to category 1 plants, with no chlorosis on the cotyledons; 7=stunted, unhealthy plants that have started wilting but still have a few green leaves at the top of the plant; and 9=plants are severely stunted and dead or dying. The experiment is considered successful if 90% of the susceptible control plants fall within category 9 and 90% of the resistant control plants fall within category 1.

Example 2. Tomato Chlorosis Virus Resistance Assays

Tomato chlorosis virus (ToCV) is a whitefly (*Bremsia tabaci*) transmitted disease. The phenotypic method described herein involves the use of *B. tabaci* carrying ToCV to test for resistance in tomato plants. Typically, *B. tabaci* are maintained in cages with whitefly-proof netting where the population is maintained on melon or eggplant plants. These whitefly populations should be free from plant virus and can be maintained in a growth chamber with a 24° C./18° C. day/night rhythm. ToCV is maintained on susceptible tomato plants by transmitting the virus every 3-4 months to fresh plants using *B. tabaci*.

Inoculum whiteflies are created by allowing non-viruliferous whitefly to feed on tomato plants infected with ToCV. Ideally this is done in the environment that the experiment will be performed in and can involve the following steps: a colony cage of non-viruliferous whitefly with about 1000 whitefly are transported to the test environment. These whiteflies are given an abundance of healthy melon or eggplants (6-8 plants) to feed for another 6 weeks. During this time the whitefly population increase. Two days before the experiment start, the feeder plants are replaced with at least 10 ToCV infected tomato plants. The melon/eggplants should be shaken above the tomato plants to ensure transfer of the whitefly to the new host plants. After 48-72 hours of virus acquisition by the whiteflies the experimental plants can be introduced.

An experiment should contain at least three replications of 5-6 plants/genotype. The resistant control can be the plants of the seed deposit described herein. An intermediate resistant control is a plant that is heterozygous for the ToCV resistance locus described herein. A susceptible control can be any tomato variety that doesn't show ToCV resistance symptoms. The experiment should ideally be performed using a complete randomized block design. Seedlings are grown to the two true leaves stage before they are introduced to the whiteflies carrying ToCV. The whiteflies are kept in proximity of the experimental plants for 48-72 hours to ensure transmission of the virus from the whiteflies to the plants. After this period a chemical treatment is used to kill the whiteflies (including eggs) to prevent the whiteflies from influencing the experimental outcome beyond ToCV transfer and to prevent spreading of the virus beyond the experiment. When the seedlings reach transplanting age, they are transplanted to the adult plant growth environment where the remainder of the experiment will be performed. After 45 days post inoculation (DPI) and 60 DPI plants are evaluated for ToCV symptoms. The following rating scale can be used: 1: No symptoms; 3: Slight mottle on old leaves; 5: Slight yellowing of old leaves and slight mottle on old and young leaves, symptoms are limited to the basal half of the plant; 7: Obvious interveinal yellowing of leaves with less than 50% of the plant affected and light yellowing of young leaves in the upper half of the plant; 9: Obvious interveinal yellowing of leaves, leaf thickening and brittleness and more than 50% of the plant is affected by symptoms. The experiment is successful if control plants show symptoms as expected, i.e. resistant scores of 1-3, intermediate resistant score of 5, susceptible scores of 7-9.

Example 3. Mapping of the Tomato Chlorosis Virus Resistance QTL on Chromosome 11

Resistance to tomato chlorosis virus (ToCV) in tomato was identified in breeding line 960744 and is derived from *Solanum chilense* line LA1932, which is available from the Tomato Genetics Resource Center at UC-Davis, California, USA. Breeding line 960744 was used to develop a ToCV resistant line to create a mapping population to map the ToCV resistance locus and develop molecular markers for tracking the locus. The ToCV resistance locus was mapped to a region at the end of chromosome 11, which overlaps with the location of the I-2 locus on chromosome 11 that confers resistance to Fol race 2. The resistance to ToCV was determined to be additive, where plants that are homozygous for the ToCV resistance allele on chromosome 11 show a resistance phenotype that is acceptable for a grower (FIG. 1). It was also observed that the plants containing the resistance locus showed sensitivity to cold during the winter months. The symptoms start as a mild purpling at the edge of the leaves and these leaves start curling upwards. These symptoms are followed by increasing severity of necrosis, which starts with a v-shaped pattern from the tip of the leaf leading to larger necrotic areas until the leaf is fully necrotic. At this stage all leaves in the top of the plant show necrosis and the plant will have stopped growing. This cold sensitivity phenotype is initially expressed in the younger leaves at the top of the plant after a period of more than 5 consecutive days where the night temperature is below 6° C.

A new mapping population to fine map the ToCV resistance locus and uncouple the cold sensitivity locus was developed using the parental lines of the former commercial hybrid 'Elenita'. One of the parents of this hybrid contains the ToCV resistance locus, while the other parent is susceptible to ToCV, but contains the I-2 gene. About 3000 $F_2$ seedlings were screened for recombination events in the ToCV resistance locus region. Plants with recombination events were selfed to fix the recombination events in the $F_3$ generation. A set of 32 families were developed and the $F_4$ generation was screened for ToCV resistance. The subsequent mapping analysis showed that the ToCV resistance locus is located between marker locus M1, a SNP marker with a [C/T] change at 54,914,243 bp on chromosome 11 of the public tomato genome map version SL2.50, and M3, a SNP marker with a [A/T] change at 55,443,272 bp on chromosome 11 of the public tomato genome map version SL2.50. This region encompasses a 0.6 cM region on chromosome 11. In addition, the ToCV resistance locus region comprises marker locus M2, a SNP marker with a [A/G] change at 55,135,473 bp on chromosome 11 of the public tomato genome map version SL2.50, which can also be used to select for the ToCV resistance locus. It was discovered that one line from the mapping population did not have a cold sensitivity phenotype. This line, designated CHI-1120-0340, is the deposited variety disclosed herein.

Example 4. Coupling the Tomato Chlorosis Virus Resistance QTL and the I-2 Locus on Chromosome 11

The I-2 locus that confers resistance to *Fusarium oxysporum* f. sp. *lycopersici* (Fol) race 2, is flanked by marker locus M1 and marker locus M4, a SNP marker with a [G/T] change at 54,895,724 bp on chromosome 11 of the public tomato genome map version SL2.50. This region on chromosome 11 therefore overlaps with ToCV resistance locus, which supports earlier breeder observations that the I-2 locus and ToCV resistance locus are linked in repulsion. Surprisingly, however, when the ToCV resistant lines from the fine-mapping population were screened for the presence of the I-2 locus using marker locus M1, it was found that two lines contained the marker allele for the I-2 gene. These lines were tested for Fol race 2 resistance in a pathology assay as described above. It was confirmed that these lines were resistant to Fol race 2 and thus contained the I-2 locus and the ToCV resistance locus in cis linkage configuration.

To select for the novel coupling event, marker locus M1 is used to identify the presence of the I-2 allele and marker loci M2 and/or M3 are used to identify the presence of the ToCV resistance allele (Table 1). When developing the coupling event, it is important to confirm that both resistances are present phenotypically in a line that is homozygous for at least one of the resistances.

TABLE 1

List of markers and favorable alleles at each marker for tracking resistance QTLs.

| Marker name | Chr. | Genetic Position (cM) | Public position SNP (bp) | Marker size (bp) | SNP position in marker (bp) | SNP Change | Favorable allele | Marker sequence (SEQ ID NO) | Fwd primer (SEQ ID NO) | Rev primer (SEQ ID NO) | Probe 1 (SEQ ID NO) | Probe 2 (SEQ ID NO) |
|---|---|---|---|---|---|---|---|---|---|---|---|---|
| M4 | 11 | 81.53 | 54,895,724 | 121 | 61 | [G/T] | G | 1 | 2 | 3 | 4 | 5 |
| M1 | 11 | 81.73 | 54,914,243 | 400 | 200 | [C/T] | C | 6 | 7 | 8 | 9 | 10 |
| M2 | 11 | 82.28 | 55,135,473 | 201 | 101 | [A/G] | G | 11 | 12 | 13 | 14 | 15 |
| M3 | 11 | 82.3 | 55,443,272 | 929 | 92 | [A/T] | T | 16 | 17 | 18 | 19 | 20 |

What is claimed is:

1. A *Solanum lycopersicum* plant comprising a recombinant chromosomal segment on chromosome 11, wherein said chromosomal segment comprises a tomato chlorosis virus (ToCV) resistance allele from *Solanum chilense* that confers to said plant an increased resistance to ToCV compared to a plant not comprising said allele, wherein said ToCV resistance allele is comprised within a genomic region flanked by marker locus M1 (SEQ ID NO:6) and marker locus M3 (SEQ ID NO:16) in said chromosomal segment, and wherein:
   (a) said chromosomal segment lacks an allele genetically linked to said ToCV resistance allele that confers cold sensitivity when present in a *Solanum lycopersicum* plant of the same genotype; or
   (b) said chromosomal segment further comprises a *Fusarium oxysporum* f. sp. *lycopersici* (Fol) race 2 resistance allele from *Solanum pimpinellifolium* that confers to said plant increased resistance to Fol race 2 compared to a plant not comprising said allele, wherein said Fol race 2 resistance allele is comprised within a genomic region flanked by marker locus M4 (SEQ ID NO:1) and marker locus M1 (SEQ ID NO:6) in said chromosomal segment, and wherein said Fol race 2 resistance allele is in cis linkage with said ToCV resistance allele,
   wherein a representative sample of seed comprising said chromosomal segment flanked by marker locus M1 and marker locus M3 has been deposited under NCMA Accession No. 202007005.

2. The plant of claim 1, wherein said plant is homozygous for said ToCV resistance allele.

3. A cell, seed, or plant part of the plant of claim 1, wherein the cell, seed, or plant part comprises said recombinant chromosomal segment.

4. The cell, seed, or plant part of claim 3, wherein a representative sample of seed comprising said chromosomal segment has been deposited under NCMA Accession No. 202007005.

5. The cell, seed, or plant part of claim 3, further defined as a seed.

6. A method of selecting a tomato plant exhibiting resistance to tomato chlorosis virus (ToCV) and *Fusarium oxysporum* f. sp. *lycopersici* (Fol) race 2, comprising:
   a) crossing the tomato plant of claim 1 with itself or with a second tomato plant of a different genotype to produce one or more progeny plants; and
   b) selecting a progeny plant comprising said chromosomal segment.

7. The method of claim 6, wherein selecting said progeny plant comprises detecting a marker locus genetically linked to said chromosomal segment.

8. The method of claim 7, wherein selecting said progeny plant comprises detecting a marker genetically linked to marker locus M4 (SEQ ID NO:1), marker locus M1 (SEQ ID NO:6), marker locus M2 (SEQ ID NO:11), or marker locus M3 (SEQ ID NO:16).

9. The method of claim 6, wherein said progeny plant is an F2-F6 progeny plant.

10. The method of claim 6, wherein producing said progeny plant comprises backcrossing.

\* \* \* \* \*

SEQUENCE LISTING

<160> NUMBER OF SEQ ID NOS: 20

<210> SEQ ID NO 1
<211> LENGTH: 121
<212> TYPE: DNA
<213> ORGANISM: Solanum pimpinellifolium

<400> SEQUENCE: 1
caattctaaa acgtattcat gatatgctgg gctcaattaa gcacactaca ctgagctgtt     60
kaaaaatgaa taagtgcata aagcaaaagt aatgaataga cataaagcaa aagatacttg    120
c                                                                    121

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
tgggctcaat taagcacact acac                                            24

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
gctttatgtc tattcattac ttttgcttta tgca                                 34

<210> SEQ ID NO 4

```
<211> LENGTH: 14
<212> TYPE: DNA
<213> ORGANISM: Artificial Sequence
<220> FEATURE:
<223> OTHER INFORMATION: Probe

<400> SEQUENCE: 4
agctgttgaa aaat                                                          14

<210> SEQ ID NO 5
<211> LENGTH: 16
<212> TYPE: DNA
<213> ORGANISM: Artificial Sequence
<220> FEATURE:
<223> OTHER INFORMATION: Probe

<400> SEQUENCE: 5
tgagctgttt aaaaat                                                        16

<210> SEQ ID NO 6
<211> LENGTH: 400
<212> TYPE: DNA
<213> ORGANISM: Solanum pimpinellifolium
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (302)..(303)
<223> OTHER INFORMATION: n is a, c, g, or t

<400> SEQUENCE: 6
tgttacttct tttcattttt aatcatgccg tgctagctca tcatcaaaca catagcatta         60
tatttaacct ccatagagaa tctaaatttt ttaaaggata acgatcacaa gttttaggaa        120
ataagtgcaa cttccattgt cacatgttat ataattctat atttctcatt gcttattggt       180
ttntgctctt accatgtttty aattcacgtc tcaattgcca ccatgtttaa tcaattgtcc      240
gtaggaagtg tttctaaggt gctgttgcta ttttacatc tgttcccgag ttcttttttt       300 tnncttttg aactttccac taaagctatt atgtcgtcca cagtgaattt tcaggtctgt       360
tgttataggc aagtctttga gatgggacta tcaagaagg                              400

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
gcaacttcca ttgtcacatg ttatataatt ctatattt                                38

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
ttcctacgga caattgatta aacatggt                                           28

<210> SEQ ID NO 9
<211> LENGTH: 17
```

```
<212> TYPE: DNA
<213> ORGANISM: Artificial Sequence
<220> FEATURE:
<223> OTHER INFORMATION: Probe

<400> SEQUENCE: 9
acgtgaattg aaacatg                                                    17

<210> SEQ ID NO 10
<211> LENGTH: 17
<212> TYPE: DNA
<213> ORGANISM: Artificial Sequence
<220> FEATURE:
<223> OTHER INFORMATION: Probe

<400> SEQUENCE: 10
acgtgaatta aaacatg                                                    17

<210> SEQ ID NO 11
<211> LENGTH: 201
<212> TYPE: DNA
<213> ORGANISM: Solanum chilense

<400> SEQUENCE: 11
tagttcaagt atttaggagt caatttggat cttgaatctc tttgcattgt ccatacaggc     60
aactaattga cttggagaaa gagctagaat tgagagaac rtctaaagca gttctgatgg    120
aagaatcgaa gaagggtcaa actgagctgt cttcggttgc aaatgatcag acgcctacta   180
ttgctgtcag tgatcagacg g                                              201

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
aggcaactaa ttgacttgga gaaaga                                          26

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
cccttcttcg attcttccat caga                                            24

<210> SEQ ID NO 14
<211> LENGTH: 18
<212> TYPE: DNA
<213> ORGANISM: Artificial Sequence
<220> FEATURE:
<223> OTHER INFORMATION: Probe

<400> SEQUENCE: 14
actgctttag atgttctc                                                   18

<210> SEQ ID NO 15
<211> LENGTH: 16
<212> TYPE: DNA
<213> ORGANISM: Artificial Sequence
<220> FEATURE:
```

<223> OTHER INFORMATION: Probe

<400> SEQUENCE: 15
tgctttagac gttctc                                                    16

<210> SEQ ID NO 16
<211> LENGTH: 929
<212> TYPE: DNA
<213> ORGANISM: Solanum chilense
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t

<400> SEQUENCE: 16
acatggagct tttaagtgtt caactattgc tcataatcaa gaaactaatg gttcgtgttt     60
gaacctaaga gggaatatct catctgatta awgttatagc tcaagagttg atttgcatan   120
atatttacgt gacaaactaa tgcacactac taattcctct atgtggagtg tttggaatct   180
gaacttctta ctagcactaa taaagggaga aaacaatata cgaaacttct aacataaaag   240
ccacagatca atctaatgna acccaaactt tttcttgttc tcccttgatt cttcagattc   300
atatgatgaa tataactcgg ataacccattt aaacatttac atacatacct cgactaagtc   360
gacggtacct nctatctccc ataagcagct aactttgttc accaagactt ggacagatga   420
aaagaaaccg tctagtattt tttctttgaa acattaacca aaatcaagaa gaatgatcag   480
tctaaaccta ttccagctat caccaaaacca ttttaataat ctctccaaga ttcctactca   540
tccataaccg aacaatagat agcaaaaatc ataccaaa gacaaaaaca aaatgaacaa     600
ttttacaaca ataccatagt aaaaagcacc acgatacact cacaaacaag gggtggagct   660
agaggaactc gaggagttca tctgaaacac tcacaaacat tcaagggcag agctagggga   720
cgcaaaacga accgcattca ctagaaaatt atagttgata tatacaagat caagatttaa   780
tntacatata atagatgctg catcctcttg gctaggagat cccacacttt ttagctccct   840
cgncgactcg aactcacaac cttagggttg agagtnatga atgtttatca nccgagcaac   900
ttccacttat ctcctcttgg cttcttcgc                                    929

<210> SEQ ID NO 17
<211> LENGTH: 27
<212> TYPE: DNA
<213> ORGANISM: Artificial Sequence

```
<220> FEATURE:
<223> OTHER INFORMATION: Primer

<400> SEQUENCE: 17
cgtgtttgaa cctaagaggg aatatct                                           27

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
agtagtgtgc attagtttgt cacgtaaa                                          28

<210> SEQ ID NO 19
<211> LENGTH: 21
<212> TYPE: DNA
<213> ORGANISM: Artificial Sequence
<220> FEATURE:
<223> OTHER INFORMATION: Probe

<400> SEQUENCE: 19
tcttgagcta taactttaat c                                                 21

<210> SEQ ID NO 20
<211> LENGTH: 19
<212> TYPE: DNA
<213> ORGANISM: Artificial Sequence
<220> FEATURE:
<223> OTHER INFORMATION: Probe

<400> SEQUENCE: 20
ttgagctata acattaatc                                                    19
```